US008754204B2

(12) United States Patent
Tanigami et al.

(10) Patent No.: US 8,754,204 B2
(45) Date of Patent: Jun. 17, 2014

(54) METHOD FOR PREPARING STOOL SAMPLE, SOLUTION FOR PREPARING STOOL SAMPLE, AND KIT FOR COLLECTING STOOL

(75) Inventors: Yasuo Tanigami, Tokyo (JP); Tomonori Nagaoka, Tokyo (JP)

(73) Assignee: Olympus Corporation, Tokyo (JP)

( * ) Notice: Subject to any disclaimer, the term of this patent is extended or adjusted under 35 U.S.C. 154(b) by 190 days.

(21) Appl. No.: 12/782,537

(22) Filed: May 18, 2010

(65) Prior Publication Data

US 2010/0248250 A1 Sep. 30, 2010

Related U.S. Application Data

(63) Continuation of application No. PCT/JP2008/071023, filed on Nov. 19, 2008.

(30) Foreign Application Priority Data

Nov. 20, 2007 (JP) .............................. P2007-300298
Mar. 26, 2008 (JP) .............................. P2008-080084

(51) Int. Cl.
*C07H 21/00* (2006.01)
*C07H 21/02* (2006.01)
(52) U.S. Cl.
USPC ....................... 536/25.42; 536/23.1; 536/25.4
(58) Field of Classification Search
USPC ................................................. 536/23.1, 25.4
See application file for complete search history.

(56) References Cited

U.S. PATENT DOCUMENTS

| | | | | |
|---|---|---|---|---|
| 3,957,436 | A | * | 5/1976 | Murray .......................... 436/513 |
| 5,670,325 | A | | 9/1997 | Lapidus et al. |
| 5,741,650 | A | | 4/1998 | Lapidus et al. |
| 5,855,913 | A | * | 1/1999 | Hanes et al. ................... 424/489 |
| 5,952,178 | A | | 9/1999 | Lapidus et al. |
| 5,952,200 | A | * | 9/1999 | Johnson et al. ............... 435/91.2 |
| 5,998,483 | A | * | 12/1999 | Camiener ...................... 514/705 |
| 6,020,137 | A | | 2/2000 | Lapidus et al. |
| 6,100,029 | A | | 8/2000 | Lapidus et al. |
| 6,143,529 | A | | 11/2000 | Lapidus et al. |
| 6,146,828 | A | | 11/2000 | Lapidus et al. |
| 6,156,505 | A | | 12/2000 | Steinbruch et al. |
| 6,203,993 | B1 | * | 3/2001 | Shuber et al. ................. 435/6.11 |
| 6,204,375 | B1 | * | 3/2001 | Lader ............................ 536/25.4 |
| 6,214,558 | B1 | | 4/2001 | Shuber et al. |
| 6,300,077 | B1 | | 10/2001 | Shuber et al. |
| 6,303,304 | B1 | | 10/2001 | Shuber et al. |
| 6,916,608 | B2 | * | 7/2005 | Berger et al. ................. 435/6.16 |
| 2002/0004201 | A1 | | 1/2002 | Lapidus et al. |
| 2002/0068292 | A1 | | 6/2002 | Kojima |
| 2002/0119469 | A1 | | 8/2002 | Shuber et al. |
| 2002/0119472 | A1 | | 8/2002 | Lapidus et al. |

FOREIGN PATENT DOCUMENTS

| | | |
|---|---|---|
| CN | 1824809 A | 8/2006 |
| JP | 6-72837 B2 | 9/1994 |
| JP | 6-265542 A | 9/1994 |
| JP | 7-120460 A | 5/1995 |
| JP | 10-503384 A | 3/1998 |
| JP | 11-511982 A | 10/1999 |
| JP | 2001-128662 A | 5/2001 |
| JP | 2002-511585 A | 4/2002 |
| JP | 2002-521071 A | 7/2002 |
| JP | 2003-153688 A | 5/2003 |
| JP | 2004-500897 A | 1/2004 |
| JP | 2004-519202 A | 7/2004 |
| JP | 2005-532824 A | 11/2005 |
| WO | 97/09600 A2 | 3/1997 |
| WO | 99/53316 A1 | 10/1999 |
| WO | 00/06780 A1 | 2/2000 |
| WO | 00/29618 A1 | 5/2000 |
| WO | 00/63358 A1 | 10/2000 |
| WO | 01/98542 A2 | 12/2001 |
| WO | 2004/033622 A2 | 4/2004 |

OTHER PUBLICATIONS

Zhang et al., A widely applicable protocol for DNA isolation from fecal samples, Biochemical Genetics 44: 503-512 (2006).*
DNeasy blood & Tissue Handbook[1] 2006.*
RNeasy Minii-Qiagen 2006.*
Merrell et al., Host-induced epidemic spread of the cholera bacterium, Nature lvol. 417 I Jun. 6, 2002 lpp. 642-646.*
Schoolnik et al., Whole Genome DNA Microarray Expression Analysis of Biofilm Development by *Vibrio cholerae* O 1 E1 Tor, Methods in Enzymology, vol. 3, 2001, pp. 1-18.*
Life Technologies, Material Safety Data Sheet for Trizol Reagent, 1999, pp. 1-12.*
International Search Report of PCT/JP2008/071023, mailing date of Dec. 22, 2008.
Supplementary European Search Report dated Nov. 10, 2010, issued in corresponding European Patent Application No. 08851485.6.
Gookin, Jody L. et al.; "Identification of Pentatrichomonas hominis in feline fecal samples by polymerase chain reaction assay"; Veterinary Parasitology, Elsevier Science, Amsterdam, NL LNKD-DOI;10.1016/J. Vetpar. 2006.10.020, vol. 145, No. 1-2, Mar. 13, 2007, pp. 11-15, XP005919833.
Verweij, Jaco J. et al.; "Real-time PCR for the detection of *Dientamoeba fragilis* in fecal samples"; Molecular and Cellular Probes, Academic Press, London, GB LNKD-DOI:10.1016/J.MCP. 2007.05.006, vol. 21, No. 5-6, Aug. 17, 2007, pp. 400-404, XP022206222.

(Continued)

*Primary Examiner* — Ardin Marschel
(74) *Attorney, Agent, or Firm* — Westerman, Hattori, Daniels & Adrian, LLP

(57) ABSTRACT

A method for preparing a stool sample without any need for complicated operations is provided which is capable of efficiently recovering a nucleic acid originating from mammalian cells, such as the cells exfoliated from the large intestine, in the stool. A solution for preparing a stool sample and a kit for stool collection are also provided. The collected stool is mixed with a solution for preparing a stool sample which has a water-soluble organic solvent as an active ingredient. A method is disclosed for recovering a nucleic acid including recovering a nucleic acid originating from indigenous enteric bacterium and a nucleic acid originating from an organism other than indigenous enteric bacterium at the same time from the stool sample prepared by the preparation method.

12 Claims, 4 Drawing Sheets

(56) References Cited

OTHER PUBLICATIONS

Verweij, Jaco J. et al.; "Simultaneous Detection and Quantification of *Ancylostoma duodenale*, Necator amercanus, and Oesophagostomum bifurcum in Fecal Samples Using Multiplex Real-Time PCR"; The American Journal of Tropical Medicine and Hygiene, Oct. 2007 LNKD-Pubmed: 17978072, vol. 77, No. 4, Oct. 2007, pp. 685-690, XP007915505.

Chinese Office Action dated May 22, 2012, issued in corresponding Chinese Patent Application No. 200880124866.6.(12 pages).

Japanese Office Action dated Nov. 5, 2013, in corresponding Japanese Application No. 2009-542570 w/English Translation. (4 pages).

* cited by examiner

METHOD FOR PREPARING STOOL SAMPLE, SOLUTION FOR PREPARING STOOL SAMPLE, AND KIT FOR COLLECTING STOOL

TECHNICAL FIELD

The present invention relates to a method for preparing a stool sample in order to efficiently recover a nucleic acid from the stool sample, a solution for preparing a stool sample, a kit for collecting stool, a stool sample prepared by the above preparation method, a method for recovering a nucleic acid from the above stool sample, and a method for analyzing nucleic acid that uses the a nucleic acid recovered by the above nucleic acid recovering method.

BACKGROUND ART

Like the case found in Europe and the United States, the number of colon cancer patients in Japan is rapidly increasing from year to year, and the colon cancer is now accounting for the major parts of the mortality caused by cancer. It is thought that this is due to the change in the eating habits of Japanese people to eat more meat, just like the people in the Western world. More specifically, about 60 thousand people are developing colon cancer every year, and also in terms of the number of deaths caused by cancer in different organs, colon cancer comes in 3rd following gastric cancer and lung cancer, and this number is expected to increase even further in the future. On the other hand, unlike other cancers, nearly 100% of colon cancer can be cured if treated at an early stage of development. Therefore, it is extremely worthwhile to select colon cancer as a subject for the screening of early stage cancers, and studies for developing examination methods for the early detection of colon cancers have been intensively conducted.

As the examination methods for the early detection of colon cancers, for example, enema examinations, colonoscopic examinations and the like have been carried out. An enema examination refers to an examination process in which barium is injected into the large intestine and caused to attach to its mucosal surface, and X-ray is irradiated thereto to perform radiography of the surface irregularities, thereby observing the surface of large intestine. On the other hand, a colonoscopic examination refers to an examination process in which the inside of a large intestine is directly observed using an endoscope. The colonoscopic examination in particular is highly sensitive and specific, and is also advantageous in that the removal of polyps or early stage cancers is possible.

However, these test methods are costly and impose a heavy burden on the subjects, and they are also associated with the risk of complications. For example, the enema examination is associated with the risks of X-ray exposure and intestinal obstruction. In addition, the colonoscopic examination is an invasive process since an endoscope is directly inserted inside the large intestine, and the endoscopic operations also require highly technical skills, and thus facilities that can provide this type of examination are limited in number. For this reason, these examination methods are not suitable for colon cancer screening of members of the general public who have no symptoms in cases such as routine checkups.

In recent years, as a primary screening method for colon cancer, a fecal occult blood test has been widely performed, which is a non-invasive process and can be performed at a low cost. The fecal occult blood test is a method for examining the presence and absence of the hemoglobin contained in stool and originating from red blood cells, thereby indirectly predicting the presence of colon cancer. The fecal occult blood test has been widely used for the following reasons: i.e., the collection and storage of stool can be conducted at normal temperatures; no special storage conditions such as refrigeration and freezing are required; and the test can be easily carried out in ordinary households and the operation therefor is highly simple and easy. However, the sensitivity of the fecal occult blood test is low at about 25%, which means that there is a relatively high risk of overlooking the presence of colon cancers. In addition, its positive predictive value is also low, and the percentage of actual colon cancer patients among the subjects that are determined to be positive in a fecal occult blood test is 10% or less. Accordingly, the test is fraught with many false positives. For this reason, there is a strong demand for the development of novel examination methods that are more reliable.

As a new examination method suited for routine checkups or the like which is noninvasive, simple and easy, and also more reliable, a test for examining the presence and absence of cancer cells or genes originated from cancer cells in stool is gaining attention. As compared to the fecal occult blood test, whereby the presence of bleeding from the gastrointestinal tract which is caused indirectly in association with the development of colon cancer is examined, this method is expected to constitute a more reliable examination method because it involves a direct examination concerning the presence and absence of cancer cells or genes originated from cancer cells.

In order to detect cancer cells or the like in stool samples with high accuracy, it is important to efficiently recover the nucleic acid originating from the cancer cells in the stool samples. The amount of nucleic acids originating from cancer cells is particularly low, and nucleic acids are also extremely prone to degradation since a large amount of digestion residues or bacterial cells are contained in stool. Therefore, in order to efficiently recover the nucleic acid, especially the nucleic acid originating from mammalian cells such as human cells, from the stool samples, it is important to prepare the stool samples so as to prevent the degradation of nucleic acids in the stool and to stably preserve the samples until the time of examination operations. As such methods for preparing stool samples, for example, there is a method in which the cancer cells exfoliated from the gastrointestinal tracts such as large intestines are isolated from the collected stool. By isolating cancer cells from stool, the adverse effects caused by the degrading enzymes originating from bacteria and the like such as proteases, DNases and RNases can be suppressed. As a method to isolate cancer cells from stool, for example, a method has been disclosed, which is a method for isolating cells and characterized by including: a) a step for cooling stool down to a temperature below its gel freezing point; and b) a step for collecting cells from the stool while maintaining the stool at a temperature below its gel freezing point, such that the stool remains substantially intact (for example, refer to Patent Document 1). As an alternative, a method has been disclosed in which stool is dispersed in a transport medium containing a protease inhibiting substance, a mucilage solubilizing agent and a bactericide at a normal ambient temperature, followed by the isolation of cells exfoliated from the large intestine (for example, refer to Patent Document 2).

On the other hand, when observing cell forms histologically and cytologically, in order to maintain the form of collected cells until the time of observation, various fixation methods such as formalin fixation and alcohol fixation have conventionally been performed. As a preservation solution that enables the long term preservation of mammalian cell samples as well as the cell observation following the preservation which takes advantage of the above fixation methods, for example, a cell solution preserving agent has been disclosed which contains an alcohol miscible with water in an amount sufficient for fixing mammalian cells, an anticoagulant in an amount sufficient for preventing the aggregation of mammalian cells in the solution, and a buffering agent that keeps the solution pH within a range from 4 to 7 (for example, refer to Patent Document 3).

Further, as a preserving solution that enables not only the histological and cytological observations of cells, but also the molecular biological analysis of proteins, nucleic acids and the like in the cells following preservation, for example, a universal collection medium containing a buffer component, at least one alcohol component, a fixative component, and a chemical agent which suppresses the degradation of at least one type of molecules selected from the group consisting of RNA, DNA and proteins (for example, refer to Patent Document 4), a non-aqueous solution containing 5 to 20% of polyethylene glycol and 80 to 95% of methanol (for example, refer to Patent Document 5), or the like has been disclosed. In addition, a composition is also disclosed which is a composition that stabilizes the cell structure and nucleic acids and contains: (a) a first substance that contains at least one type of alcohol or ketone and is capable of precipitating or denaturing proteins; and (b) a second promoting substance which promotes the infusion of the first substance into at least one cell (for example, refer to Patent Document 6).

[Patent Document 1] Published Japanese Translation No. Hei 11-511982 of PCT International Publication

[Patent Document 2] Published Japanese Translation No. 2004-519202 of PCT International Publication

[Patent Document 3] Japanese Unexamined Patent Application, First Publication No. 2003-153688

[Patent Document 4] Published Japanese Translation No. 2004-500897 of PCT International Publication

[Patent Document 5] Published Japanese Translation No. 2005-532824 of PCT International Publication

[Patent Document 6] Japanese Unexamined Patent Application, First Publication No. 2001-128662

[Patent Document 7] Japanese Patent Application, Second Publication No. Hei 6-72837

DISCLOSURE OF INVENTION

Problems to be Solved by the Invention

In the method for isolating cancer cells from stool as disclosed in the above-mentioned Patent Document 1, cells are isolated while cooling the stool samples. If this isolation procedure is conducted without a cooling process, accurate detection results cannot be achieved due to the deterioration of stool samples or the like. Accordingly, it is important to cool the stool samples immediately after the stool collection in order to effectively prevent the degradation of stool samples. However, when the stool collection is carried out in ordinary households for a routine checkup or the like, it is very difficult and thus not realistic to cool the stool sample quickly after the collection thereof.

In addition, although it is possible to freeze the stool samples in order to prevent the deterioration thereof, it is necessary to melt the frozen stool samples before the examination, and thus the operations become complicated.

In the method for dispersing stool in a transport medium as disclosed in the above-mentioned Patent Document 2, although it is possible to prepare and preserve the stool samples at room temperature without involving any cooling operations due to the addition of a bactericide or the like, isolation of the cells, which are exfoliated from the large intestine, from stool is a complicated procedure. Further, it is also possible that the cells exfoliated from the large intestine and the nucleic acids or the like originating from the cells exfoliated from the large intestine are degraded by the nucleases and proteolytic enzymes originating from bacterial cells that are broken down by the bactericide or the like, as a result of which the accuracy for the colon cancer detection may decline. In addition, because the cells are preserved while being kept alive, the molecular profiling thereof such as the gene expressions in the cells exfoliated from the large intestine may also be altered over time due to the adverse effects caused by the components in the medium such as antibiotics or the like.

On the other hand, by using preservation solutions as described in the methods disclosed in the above-mentioned Patent Documents 3, 4 and 5, cells can be stably preserved at room temperature. However, these preservation solutions are usually used by targeting the isolated cells. Hence, it is difficult to use them directly for the biological samples, such as stool, which contain various types of substances. By using such preservation solutions to the cells isolated from stool which are exfoliated from the large intestine, the cells can be preserved for a long time without altering the molecular profiling thereof such as gene expressions of the cells. However, because the number of cells in stool which are exfoliated from the large intestine is scarce, it has been difficult to extract a sufficient amount of nucleic acids from the cells for the analysis. Further, the composition disclosed in the above-mentioned Patent Document 6 which stabilizes the cell structure and nucleic acids may stably preserve the nucleic acids which are mainly originating from bacteria in vaginal swab samples. However, there is absolutely no description on whether the composition may stably preserve the nucleic acids originating from mammalian cells having different structures from those of bacteria and which are also obtained in far less amounts than those of bacteria. Furthermore, there is absolutely no description on whether nucleic acids may be stably preserved when the composition is used for stool that contains a large amount of digestion residues or the like, unlike the vaginal swab samples.

An object of the present invention is to provide a method for preparing a stool sample, without any need for complicated operations, which is capable of efficiently recovering nucleic acids or the like originating from mammalian cells, such as the cells exfoliated from the large intestine, in the stool; a solution for preparing a stool sample and a kit for stool collection which are used in the above method; and a method for recovering and analyzing the nucleic acids in stool using the stool sample prepared by the above method.

Means for Solving the Problems

As a result of intensive and extensive studies in order to solve the above-mentioned problems, the inventors of the present invention found that a stool sample may be prepared, which is capable of efficiently recovering the nucleic acid contained in the stool, by mixing the collected stool with a solution for preparing a stool sample having a water-soluble organic solvent as an active ingredient; and the nucleic acid contained in trace amounts and originating from an organism other than indigenous enteric bacteria may be recovered highly efficiently by recovering the nucleic acid originating from an organism, other than indigenous enteric bacteria, such as mammalian cells which are detection targets, and the nucleic acid originating from indigenous enteric bacteria which are contained in the stool in large amounts at the same time, thereby leading to completion of the present invention.

In other words, the present invention includes the following aspects.

(1) A method for preparing a stool sample which is a method for preparing a stool sample in order to efficiently recover a nucleic acid from the stool sample, the method characterized in that the stool collected from a subject is mixed with a solution having a water-soluble organic solvent as an active ingredient.

(2) The method for preparing a stool sample according to the aspect (1) characterized in that in terms of a mixing ratio of the stool and the solution, a volume of the solution is 1 or more relative to 1 volume of the stool.

(3) The method for preparing a stool sample according to the aspect (1) or (2) characterized in that the water-soluble organic solvent is a water-soluble alcohol and/or a ketone.

(4) The method for preparing a stool sample according to any one of the aspects (1) to (3) characterized in that a concentration of the water-soluble organic solvent in the solution is within a range from 30% to 100%.

(5) The method for preparing a stool sample according to the aspect (3) or (4) characterized in that the water-soluble alcohol is at least one alcohol selected from the group consisting of ethanol, propanol and methanol.

(6) The method for preparing a stool sample according to the aspect (5) characterized in that the water-soluble alcohol is ethanol.

(7) The method for preparing a stool sample according to the aspect (3) or (4) characterized in that the ketone is acetone and/or methyl ethyl ketone.

(8) The method for preparing a stool sample according to the aspect (1) or (2) characterized in that the water-soluble organic solvent is an aldehyde.

(9) The method for preparing a stool sample according to the aspect (8) characterized in that a concentration of the aldehyde in the solution is within a range from 0.01 to 30%.

(10) The method for preparing a stool sample according to any one of the aspects (1) to (9) characterized in that the solution further includes a surface active agent.

(11) The method for preparing a stool sample according to any one of the aspects (1) to (10) characterized in that the solution further includes a colorant.

(12) A solution for preparing a stool sample which is a solution used for efficiently recovering a nucleic acid from the stool sample, the solution characterized by having a water-soluble organic solvent as an active ingredient.

(13) A solution for preparing a stool sample which is a solution used for efficiently recovering a nucleic acid from the stool sample, the solution characterized by including a water-soluble organic solvent having a concentration within a range from 30% to 100%.

(14) A kit for collecting stool characterized by including a stool collection container and a solution having a water-soluble organic solvent as an active ingredient, wherein the stool collection container includes the above solution for preparing a stool sample.

(15) The kit for collecting stool according to the aspect (14) characterized in that a concentration of the water-soluble organic solvent in the solution is within a range from 30% to 100%.

(16) A stool sample prepared by the method for preparing a stool sample of any one of the aspects (1) to (11).

(17) A method for recovering a nucleic acid characterized by including a step for mixing stool collected from a subject with a solution having a water-soluble organic solvent as an active ingredient so as to prepare a mixture; and a step for recovering a nucleic acid originating from indigenous enteric bacteria and a nucleic acid originating from an organism other than indigenous enteric bacteria, from the mixture at the same time.

(18) The method for recovering a nucleic acid according to the aspect (17) characterized in that the nucleic acid originating from an organism other than indigenous enteric bacteria is a nucleic acid originating from a mammalian cell.

(19) The method for recovering a nucleic acid according to the aspect (17) or (18) wherein the step for recovering a nucleic acid includes (a) a step for denaturing proteins in the stool sample and thereby eluting a nucleic acid from indigenous enteric bacteria and an organism other than indigenous enteric bacteria in the stool sample; and (b) a step for recovering the nucleic acid eluted in the above step (a).

(20) The method for recovering a nucleic acid according to the aspect (19) further including, following the above step (a) and prior to the above step (b), (c) a step for removing the protein denatured in the above step (a).

(21) The method for recovering a nucleic acid according to the aspect (19) or (20) wherein denaturing of a protein in the step (a) is carried out using at least one material selected from the group consisting of a chaotropic salt, an organic solvent and a surface active agent.

(22) The method for recovering a nucleic acid according to the aspect (21) wherein the organic solvent is phenol.

(23) The method for recovering a nucleic acid according to any one of the aspects (20) to (22) wherein removal of denatured proteins in the step (iii) is carried out using chloroform.

(24) The method for recovering a nucleic acid according to any one of the aspects (19) to (23) wherein recovering of a nucleic acid in the step (b) includes (b1) a step for making the nucleic acid that are eluted in the step (a) to adsorb to an inorganic substrate; and (b2) a step for eluting the nucleic acid adsorbed in the above step (b1) from the inorganic substrate.

(25) The method for recovering a nucleic acid according to any one of the aspects (19) to (24) wherein further comprising, prior to the step (i), (iv) recovering a solid component from the stool sample.

(26) A method for analyzing a nucleic acid comprising conducting an analysis of a nucleic acid originating from mammalian cells using a nucleic acid recovered from a stool sample by use of the method for recovering a nucleic acid of any one of the aspects (17) to (25).

(27) The method for analyzing a nucleic acid according to the aspect (26) wherein the mammalian cell is a gastrointestinal tract cells.

(28) The method for analyzing a nucleic acid according to the aspect (27) wherein the gastrointestinal tract cell is a cell exfoliated from a large intestine.

(29) The method for analyzing a nucleic acid according to any one of the aspects (26) to (28) wherein the nucleic acid originating from a mammalian cell is a marker indicating a neoplastic transformation.

(30) The method for analyzing a nucleic acid according to any one of the aspects (26) to (28) wherein the nucleic acid originating from a mammalian cell is a marker indicating an inflammatory gastrointestinal disease.

(31) The method for analyzing a nucleic acid according to the aspect (26) wherein the analysis is an RNA analysis and/or a DNA analysis.

(32) The method for analyzing a nucleic acid according to the aspect (31) wherein the RNA analysis is at least one analysis of an analysis for insertion, deletion, substitution, duplication or inversion of an RNA base or for a splicing variant, an mRNA expression analysis and a functional RNA analysis.

(33) The method for analyzing a nucleic acid according to the aspect (31) wherein the DNA analysis is at least one analysis selected from a mutation analysis and an analysis of epigenetic changes.

(34) The method for analyzing a nucleic acid according to the aspect (33) wherein the mutation analysis is an analysis for at least one mutation of an insertion, deletion, substitution, duplication or inversion of a base.

(35) The method for analyzing a nucleic acid according to the aspect (33) wherein the mutation analysis is a mutation analysis of a K-ras gene.

(36) The method for analyzing a nucleic acid according to the aspect (33) wherein the analysis of epigenetic changes is at least one analysis of a DNA methylation analysis and a DNA demethylation analysis.

Effect of the Invention

By using the method for preparing a stool sample according to the present invention, a stool sample can be prepared from which nucleic acids can be efficiently recovered. In addition, by using the method for preparing a stool sample according to the present invention, the nucleic acids contained in the stool sample in a relatively small amount which are originating from organisms other than indigenous enteric bacterium such as mammalian cells can be stably maintained so as to be preservable for a long time at room temperature. In particular, because the procedures from the stool collection to the preparation, preservation and transport of stool samples can be carried out in a simple and easy manner at room temperature, the method is highly suitable for the preparation of stool samples for the screening test performed in routine checkups or the like. Moreover, since the method does not require a complicated operation of isolating organisms or the cells thereof which are the detection targets, such as mammalian cells, from the stool samples, even when handling numerous samples, the level of labor and cost required can be effectively reduced. In particular, by using the kit for collecting stool according to the present invention, it becomes possible to prepare a stool sample even more easily.

Furthermore, in the method for recovering a nucleic acid according to the present invention, the nucleic acid originating from an organism other than indigenous enteric bacterium and a nucleic acid originating from indigenous enteric bacterium are recovered at the same time from the stool sample prepared by the method for preparing a stool sample according to the present invention. Accordingly, the nucleic acid originating from mammalian cells or the like which are obtained in far less amounts than those originating from indigenous enteric bacterium can be recovered at considerably high efficiency, and the markers for specific diseases such as colon cancer can be detected with considerably high sensitivity and accuracy by conducting nucleic acid analyses using the nucleic acid recovered in such a manner.

As described above, by using the method for preparing a stool sample according to the present invention, the method for recovering a nucleic acid from the stool samples prepared by the above preparation method, and the method for analyzing a nucleic acid using the nucleic acid recovered by the above nucleic acid recovering method, the nucleic acid in stool can be analyzed with high sensitivity as well as high accuracy. Therefore, they are expected to make great contributions to the early detection or diagnosis of various symptoms and diseases, represented by the colon cancer, observations of the course of treatment, pathological studies of other abnormal conditions of patients, or the like.

DESCRIPTION OF THE REFERENCE SYMBOLS

Figure 1:
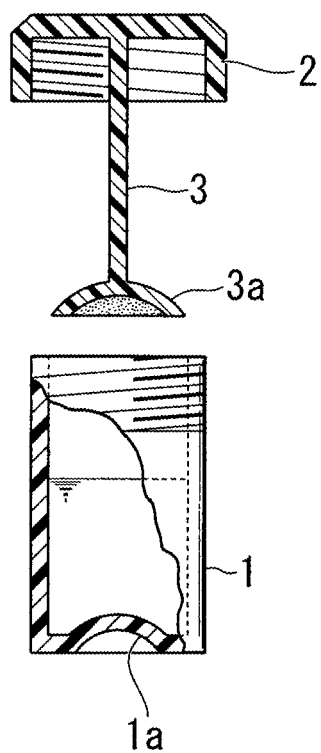
FIG. 1 is a diagram showing one aspect of a stool collection container which can be used for a kit for collecting stool according to the present invention.

1: Container body; 1a: Protruded portion; 2: Lid; 3: Stool collection rod; 3a: Cup; S: Solution for preparing stool sample; 11: Container body; 12: Lid; 13: Stool collection rod; 13a: Orifice; 13b: Movable lid; 15: Bag; E: Stool

BEST MODE FOR CARRYING OUT THE INVENTION

A method for preparing a stool sample according to the present invention is a method for preparing a stool sample in order to efficiently recover a nucleic acid from the stool sample, and is characterized in that the stool collected from a subject is mixed with a solution having a water-soluble organic solvent as an active ingredient. By mixing stool with a water-soluble organic solvent, the loss of a nucleic acid contained in the stool due to decomposition or the like can be suppressed down to the minimum level. Therefore, a nucleic acid can be efficiently recovered from the stool samples. It is considered that the effects of such highly efficient nucleic acid recovery by water-soluble organic solvents, that is, the effects to prevent the decomposition of a nucleic acid and to stably retain and recover a nucleic acid at high efficiency are achieved due to the following reasons. Dehydration caused by the water-soluble organic solvent component considerably reduces the cellular activities of living cells apart from the resident bacteria in the intestine which are the targets of detection such as mammalian cells and viruses, as well as the cellular activities of the resident bacteria in the intestine, thereby suppressing the degradation of a nucleic acid over time. Moreover, protein denaturation caused by the water-soluble organic solvent component considerably reduces the activities of various degrading enzymes such as proteases, DNases, and RNases in the stool.

The aforementioned solution, that is, the solution for preparing a stool sample according to the present invention which is used in the method for preparing a stool sample according to the present invention contains a water-soluble organic solvent as an active ingredient. Biological samples such as stool usually contain a large amount of water. Therefore, by containing a water-soluble organic solvent as an active ingredient which can be mixed with a highly water-soluble solvent or water at a given ratio, the solution for preparing a stool sample according to the present invention can be rapidly mixed with a stool sample, thereby further increasing the efficiency of nucleic acid recovery.

In the present invention, the term "water-soluble organic solvent" refers to alcohols, ketones, aldehydes, and combinations of these solvents, and these solvents have straight chain structures and are in a liquid state at a temperature close to room temperature, for example, from 15° C. to 40° C. Note that the "water-soluble organic solvent" in the present invention does not include organic acids. By containing a water-soluble organic solvent with a straight chain structure as an active ingredient rather than containing a water-soluble organic solvent with a cyclic structure, such as a benzene ring, as an active ingredient, a mixing process with a stool sample can be swiftly conducted. In general, the organic solvents having a cyclic structure therein readily separates from water, and thus hardly mixes with stool, making it difficult to achieve a high efficiency for the nucleic acid recovery. This is because even when a solvent which is soluble in water to a certain extent is used, in order to homogeneously disperse stool therein, the sample needs to be mixed vigorously or be heated in many cases. In order to make the mixing of the organic solvents having a cyclic structure with stool easier, it is also possible to prepare a mixed solution of organic solvents and water in advance, followed by the mixing of stool with the mixed solution. However, for preparing such a mixed solution, the organic solvents having a cyclic structure and water need to be mixed vigorously or be heated in many cases, which is not preferable.

In the solution for preparing a stool sample according to the present invention, the water-soluble organic solvent preferably has a water solubility of 12% by weight or more, more preferably a water solubility of 20% by weight or more, still more preferably a water solubility of 90% by weight or more, and it is most preferable that the water-soluble organic solvent be one which can be mixed with water at a given ratio. Examples of the water-soluble organic solvent which can be mixed with water at a given ratio include methanol, ethanol, n-propanol, 2-propanol, acetone and formaldehyde.

The water-soluble organic solvent contained in the solution for preparing a stool sample according to the present invention is not particularly limited as long as it satisfies the above definition and is a solvent capable of increasing the efficiency of nucleic acid recovery. Examples of the water-soluble organic solvent include alcohols which are water-soluble alcohols such as methanol, ethanol, propanol, butanol and mercaptoethanol; ketones such as acetone and methyl ethyl ketone (having a water solubility of 90% by weight); aldehydes such as acetaldehyde (acetyl aldehyde), formaldehyde (formalin), glutaraldehyde, paraformaldehyde and glyoxal. Propanol may be either n-propanol or 2-propanol. Further, butanol may be either 1-butanol (having a water solubility of 20% by weight) or 2-butanol (having a water solubility of 12.5% by weight). The water-soluble organic solvent used in the present invention is preferably a water-soluble alcohol, acetone, methyl ethyl ketone or formaldehyde. This is because these solvents have sufficiently high water solubility. The water-soluble organic solvent is more preferably a water-soluble alcohol, and still more preferably ethanol, propanol or methanol. Ethanol in particular is the safest and can easily be handled in general households, and is thus particularly useful in the screening test for routine checkups or the like.

The concentration of water-soluble organic solvent in the solution for preparing a stool sample according to the present invention is not particularly limited as long as it is a concentration capable of increasing the efficiency of nucleic acid recovery, and is thus can be appropriately determined depending on the types of water-soluble organic solvent or the like. For example, when a water-soluble alcohol or ketone is used as an active ingredient, the concentration of water-soluble organic solvent in the solution for preparing a stool sample according to the present invention is preferably at least 30% and not more than 100%. If the concentration of water-soluble organic solvent is sufficiently high, when stool and the solution for preparing a stool sample are mixed, the water-soluble organic solvent component rapidly penetrates into the mammalian cells or indigenous enteric bacteria in the stool, thereby swiftly increasing the efficiency of nucleic acid recovery.

Note that in the present invention and in the present description, "%" refers to "volume %", unless otherwise specified.

In particular, when a water-soluble alcohol is used as an active ingredient, the concentration of water-soluble organic solvent in the solution for preparing a stool sample according to the present invention is preferably at least 30%, more preferably at least 50%, still more preferably within a range from 50 to 80%, and most preferably within a range from 60 to 70%. Even when a small amount of solution for preparing a stool sample is used with respect to stool having a high water content, as the concentration of water-soluble organic solvent increases, a sufficiently high efficiency of nucleic acid recovery can be achieved.

Further, when acetone or methyl ethyl ketone is used as an active ingredient, the concentration of water-soluble organic solvent in the solution for preparing a stool sample according to the present invention is preferably at least 30% and not more than 100%, and within this range, more preferably at least 60%, and still more preferably at least 80%. Alternatively, when acetaldehyde, formaldehyde, glutaraldehyde, paraformaldehyde or glyoxal is used as an active ingredient, the concentration of water-soluble organic solvent in the solution for preparing a stool sample according to the present invention is preferably at least 0.01% and not more than 30%, more preferably at least 0.03% and not more than 10%, and still more preferably at least 3% and not more than 5%. Aldehydes can increase the efficiency of nucleic acid recovery even at lower concentrations as compared to those of alcohols and ketones.

In addition, the water-soluble organic solvent used in the present invention may only contain a single type of water-soluble organic solvent or may be a mixed solution of two or more types of water-soluble organic solvents. For example, the water-soluble organic solvent may be a mixed solution of two or more types of alcohols, or may be a mixed solution of an alcohol and another type of water-soluble organic solvent. Since the efficiency of nucleic acid recovery can be increased even further, it is also preferable that the water-soluble organic solvent be a mixed solution of an alcohol and acetone.

Although the volume of solution for preparing a stool sample to be mixed with the collected stool is not particularly limited, in terms of the mixing ratio of the stool and the solution for preparing a stool sample, the volume of the solution for preparing a stool sample is preferably 1 or more, relative to 1 volume of the stool. This is because when stool is collected in a stool collection container that contains the solution for preparing a stool sample, if the volume of the solution for preparing a stool sample is equivalent to or more than the volume of the stool, the stool can be completely immersed in the solution, and thus the effects of the present invention can be achieved. For example, when the volume of stool and that of the solution for preparing a stool sample are equivalent, it becomes possible to reduce the weight and size of the stool collection container that contains the solution for preparing a stool sample. On the other hand, by mixing the solution for preparing a stool sample with stool, five times or more of the volume of the stool, the stool can be effectively dispersed in the solution, and the adverse effects caused by the decline of water-soluble alcohol concentration due to the water contained in the stool can also be suppressed. In view of achieving a good balance between the two effects; i.e., the weight reduction of a stool collection container that contains the solution for preparing a stool sample, and the improvement of stool dispersibility, the mixing ratio of the stool and the solution for preparing a stool sample is more preferably from 1:1 to 1:20, still more preferably from 1:3 to 1:10, and most preferably about 1:5.

Although the volume of solution for preparing a stool sample to be mixed with the collected stool is not particularly limited, the volume is preferably within a range from 100 μl to 100 ml, and more preferably within a range from 1 ml to 10 ml. When the amount of solution is less than the above-mentioned volume, stool and the solution do not mix in an efficient manner. On the other hand, when the amount of solution is more than the above-mentioned volume, the size of the stool collection container increases, which makes it difficult to handle.

It should be noted that the stool supplied for the method for preparing a stool sample according to the present invention is not particularly limited as long as it is originated from an animal (a subject), but is preferably one that originated from a mammal, and is more preferably one that originated from a human being. For example, the stool is preferably stool of a human being collected for the routine checkups, diagnosis or the like, but may be stool of a domestic animal, a wild animal, or the like. Moreover, the stool may be one which has been preserved for a certain period of time following the collection thereof, but is preferably one which has just been collected. Furthermore, the stool is preferably collected immediately after the excretion thereof, but may be collected after a certain period of time following the excretion thereof.

The amount of the stool supplied for the method for preparing a stool sample according to the present invention is not particularly limited, but is preferably within a range from 10 mg to 1 g. When the amount of stool is too large, the time required for collecting operations increases and the size of a stool collection container also becomes too large, and thus it is possible that the handling properties or the like may be impaired. On the other hand, when the amount of stool is too small, because the number of mammalian cells, such as the cells exfoliated from the large intestine, contained in the stool is too small, necessary amounts of a nucleic acid cannot be recovered, and thus it is possible that the level of analytical accuracy for the target nucleic acid may be reduced. In addition, because stool is heterogeneous, in other words, because various kinds of components are present therein in a nonuniform manner, in order to avoid the adverse effects caused by the localization of mammalian cells, at the time of stool collection, it is preferable to collect a sample from various parts of the stool.

The solution for preparing a stool sample can be obtained by appropriately diluting a water-soluble organic solvent so as to adjust to a desired concentration. The solvent used for the dilution is not particularly limited, but is preferably a buffer solution such as water and phosphate buffered saline (PBS). In addition, the solution for preparing a stool sample may contain any components other than the water-soluble organic solvent as long as they do not impair the efficiency of nucleic acid recovery achieved due to the water-soluble organic solvent component. For example, the solution may contain a chaotropic salt or a surface active agent. By including a chaotropic salt or a surface active agent, the cell activity or enzyme activity of various degrading enzymes in stool can be inhibited more effectively. Examples of the chaotropic salt to be included in the solution for preparing a stool sample include guanidine hydrochloride, guanidine isothiocyanate, sodium iodide, sodium perchlorate and sodium trichloroacetate.

The surface active agent to be included in the solution for preparing a stool sample is preferably a nonionic surface active agent. Examples of nonionic surface active agent include TWEEN 80 (polyoxyethylene sorbitan monooleate), CHAPS (3-[3-cholamidopropyl dimethylammonio]-1-propanesulfonate), TRITON X-100 (polyethylene glycol p-(1,1,3,3-tetramethylbutyl)-phenyl ether), and TWEEN 20 (polyoxyethylene sorbitan monolaurate). The type and concentration of chaotropic salt or surface active agent are not particularly limited as long as it is a component with a concentration capable of increasing the efficiency of nucleic acid recovery, and is thus can be appropriately determined depending on the amount of stool or the methods for recovering and analyzing a nucleic acid employed afterwards.

In addition, a colorant may be added to the solution for preparing a stool sample, where appropriate. By coloring the solution for preparing a stool sample, various effects can be achieved, such as the prevention of accidental swallowing and the lightening of stool color. The colorant is preferably a coloring agent used as a food additive that is blue, green, or the like. Preferred examples include Fast Green FCF (Green No. 3), Brilliant Blue FCF (Blue No. 1) and indigo carmine (Blue No. 2). Further, a plurality of colorants may be added as a mixture, or a single colorant may be added.

It is preferable that the mixing of stool and the solution for preparing a stool sample be performed quickly. This is because by quickly dispersing stool in the solution for preparing a stool sample, the water-soluble organic solvent component rapidly penetrates into the cells in the stool, thereby swiftly increasing the efficiency of nucleic acid recovery. Note that the method for mixing stool and the solution for preparing a stool sample is not particularly limited as long as it is a mixing method involving physical operations. For example, the mixing may be carried out by putting the collected stool in a sealable container in which the solution for preparing a stool sample has been added in advance, followed by inversion of the container or shaking of the container using a shaker, such as a vortex mixer. In addition, stool and the solution for preparing a stool sample may be mixed under the presence of particles for mixing.

It is preferable to adopt a mixing method that uses a shaker or particles for mixing since the mixing can be rapidly carried out. In particular, by using a stool collection container in which particles for mixing are added in advance, the mixing can be rapidly conducted even in environments with no special equipment such as general households.

The particles for mixing are not particularly limited as long as they are formed of compositions that do not impair the efficiency of nucleic acid recovery achieved due to the water-soluble organic solvent component, and are particles having hardness and specific gravity sufficient to rapidly disperse stool in the solution for preparing a stool sample when colliding with the stool. The particles may be composed of one type of material or may be composed of 2 or more types of materials. Examples of such particles for mixing include particles composed of glass, ceramics, plastics, latices, metals, or the like. In addition, the particles for mixing may be magnetic particles or nonmagnetic particles.

In particular, when analyzing, as the target nucleic acid, the nucleic acid originated from an organism other than indigenous enteric bacterium, in other words, the nucleic acid contained in a stool sample in a relatively small amount as compared to the nucleic acid originated from indigenous enteric bacterium which are contained therein in a large amount, it is preferable to prepare a stool sample using the solution for preparing a stool sample according to the present invention. The nucleic acids in stool are gradually lost over time following the stool excretion due to degradation or the like. For this reason, when the target nucleic acids are those that are present in stool in a small amount, if an analysis is performed using a stool sample in which the degradation of nucleic acids has already taken place, it may not be possible to recover a sufficient amount of target nucleic acids for the analysis. Accordingly, it is highly probable that the results would appear negative (i.e., the target nucleic acids are absent in the stool), even if the target nucleic acids were present in the stool immediately after the stool excretion. By preparing a stool sample using the solution for preparing a stool sample according to the present invention, the nucleic acids in the stool can be stably preserved, as a result of which the nucleic acids in the stool can be efficiently recovered even if they are present therein in a small amount, thereby improving the reliability of nucleic acid analysis.

Examples of the above-mentioned nucleic acids originating from an organism other than indigenous enteric bacterium include nucleic acids originating from mammalian cells, such as nucleic acids originating from cancer cells, and nucleic acids from the infected cells of an initial stage or later stage which are originating from those that caused the infectious disease, such as hepatitis viruses. In addition, the nucleic acids may be originating from parasites.

Note that in the present invention, the term "indigenous enteric bacterium/bacteria" refers to the bacterial cells which are relatively abundant in stool and are usually living inside the intestines of animals such as humans. Examples of such indigenous enteric bacteria include obligate anaerobes such as those belonging to the genera of *Bacteroides, Eubacterium, Bifidobacterium* and *Clostridium*; and facultative anaerobes such as those belonging to the genera of *Escherichia, Enterobacter, Klebsiella, Citrobacter* and *Enterococcus*.

Further, such high efficiency for the nucleic acid recovery due to the water-soluble organic solvent component is not particularly affected adversely by temperature conditions as long as sufficient amount of water-soluble organic solvent is present. Accordingly, when employing the method for preparing a stool sample according to the present invention at room temperature (in other words, a temperature at which the stool collection is usually carried out), the loss of nucleic acids in the stool can be reduced. In addition, even when the prepared stool sample is stored or transported at room temperature, the nucleic acids in the stool sample can be stably preserved. Note that the stool sample is preferably preserved at no more than 50° C. This is because a long term preservation of the stool sample under high temperature conditions reduces the concentration of water-soluble organic solvent in the stool sample due to volatilization or the like, and thus the concentration may become lower than a concentration sufficient for increasing the efficiency of nucleic acid recovery.

A stool sample prepared by the method for preparing a stool sample according to the present invention, that is, the stool sample of the present invention, can preserve the nucleic acids in the stool more stably, in particular, the nucleic acids originating from mammalian cells which are present in the stool only in a relatively small amount, due to the dehydration and denaturing of proteins by the water-soluble organic solvent. For this reason, if a stool sample is prepared using the preparation method of the present invention, not only when the stool sample immediately after the preparation thereof is used for the analysis of nucleic acids, but also when the stool sample which has been preserved for a long time or being transported is used for the analysis, it is expected that highly reliable analytical results can be achieved. In particular, the nucleic acids in stool, especially the nucleic acids originating from mammalian cells can be stably preserved for a long time at room temperature, while suppressing the changes over time with respect to the molecular profiling of the mammalian cells, such as the cells exfoliated from the large intestine, contained in the stool, to a minimal level. Therefore, by preparing the collected stool using the preparation method of the present invention, even when it takes a certain period of time from the stool collection to the nucleic acid analysis or when the stool collection is performed in one place followed by the nucleic acid analysis in another, such as the case of screening test for the routine checkups or the like, it is possible to preserve or transport the stool sample while suppressing the degradation of nucleic acids, in particular, RNA which is especially prone to break down. In addition, the stool sample can be preserved or transported in a simple and easy manner at a low cost without providing any special equipment for refrigeration or freezing, or setting temperature conditions for preservation.

The stool sample of the present invention can be provided for various nucleic acid analyses just like other biological samples containing nucleic acids. It is particularly preferable that the stool sample be provided for the nucleic acid analysis in order to examine the cancer development or the incidence of infectious diseases of which early detection is highly crucial. In addition, it is also preferable that the stool sample be provided in order to examine the development of inflammatory diseases such as colitis, enteritis, gastritis and pancreatitis. Alternatively, the stool sample may also be provided for the examinations of elevated lesions such as polyps, or the examinations of diseases of large intestine, small intestine, stomach, liver, gall bladder and bile duct such as gastric ulcer.

It is possible to examine the development of cancers, such as colon cancer and pancreatic cancer, for example, by detecting and analyzing the nucleic acids originating from cancer cells, in other words, the nucleic acids that are carrying mutations, from the stool sample. In addition, by examining whether the nucleic acids originating from biological agents causing the infectious diseases, such as the nucleic acids originating from viruses or the nucleic acids originating from parasites, can be detected or not from the stool sample, it is possible to examine the development of infectious diseases or the presence and absence of parasites. In particular, by using the stool sample for the detection of biological agents excreted in the stool, such as hepatitis A and E viruses, a test for infectious diseases can be carried out in a noninvasive, simple and easy manner. In addition, by examining whether the nucleic acids originating from pathogenic bacteria other than indigenous enteric bacteria, for example, bacteria causing food poisoning such as enterohemorrhagic *Escherichia coli* O-157 strain, can be detected or not, development of microbisms can also be tested.

It is particularly preferable to detect a marker indicating neoplastic transformation or a marker indicating an inflammatory gastrointestinal disease. Examples of the marker indicating neoplastic transformation include conventionally known cancer markers, such as carcinoembryonic antigen (CEA) and sialyl Tn antigen (STN), and the presence and absence of mutations in the APC gene, p53 gene, K-ras gene, or the like. Further, detection of methylation of the genes, such as p16, hMLHI, MGMT, p14, APC, E-cadherin, ESR1 and SFRP2, is also useful as a diagnostic marker for colon diseases (for example, refer to Lind et al., "A CpG island hypermethylation profile of primary colorectal carcinomas and colon cancer cell lines" Molecular Cancer, 2004, Vol. 3, No. 28). In addition, it has already been reported that the DNA originating from *Helicobacter pylori* in the stool sample may be used as a marker for gastric cancer (for example, refer to Nilsson et al., Journal of Clinical Microbiology, 2004, Vol. 42, No. 8, pp. 3781-3788). Meanwhile, the Cox-2 gene or the like, for example, is known as a marker indicating inflammatory gastrointestinal disease.

Since nucleic acids can be recovered highly efficiently from the stool sample prepared by the preparation method of the present invention, the sample is highly suitable, not only for the analysis of nucleic acids originating from indigenous enteric bacteria which are present in the stool in large numbers, but also for the analysis of nucleic acids originating from mammalian cells which are present in a small amount. Since the sample is formed of stool, it is preferably used for the analysis of nucleic acids originating from cells of gastrointestinal tracts, such as the large intestine, small intestine and stomach, and it is particularly preferable that the nucleic acids originating from cells exfoliated from the large intestine be analyzed using the sample.

Various kinds of materials are present in the stool sample, and a large number of substances which may become inhibiting factors in the nucleic acid analyses are also present therein. For this reason, it is possible to further improve the analytical accuracy by first recovering the nucleic acids from the stool sample and then performing the nucleic acid analyses using the recovered nucleic acids. The method for recovering nucleic acids from stool samples is not particularly limited, and any type of method may be adopted as long as it is a method generally used when recovering nucleic acids from samples. The stool sample of the present invention contains the nucleic acid originating from an organism other than indigenous enteric bacterium, such as mammalian cells (hereafter, may be referred to as "mammalian cells or the like"), and the nucleic acid originating from indigenous enteric bacterium. In the nucleic acid recovery from stool samples, although the nucleic acids originating from mammalian cells or the like and the nucleic acids originating from indigenous enteric bacteria may be recovered separately, it is particularly preferable to recover them at the same time. By recovering the nucleic acids originating from mammalian cells or the like and the nucleic acids originating from indigenous enteric bacteria at the same time, as a result of the nucleic acids originating from indigenous enteric bacteria, which are highly abundant in stool, functioning as a carrier, the nucleic acids originating from mammalian cells or the like which are present in small numbers can be recovered more efficiently, as compared to the cases where the nucleic acids are recovered following the isolation of mammalian cells or the like from the stool. Note that the nucleic acids recovered from stool samples may be DNA, RNA, or a mixture of DNA and RNA.

For example, the nucleic acids originating from mammalian cells or the like and the nucleic acids originating from indigenous enteric bacteria can be recovered at the same time from the stool sample of the present invention by performing, as a step (a), denaturing of proteins in the stool sample of the present invention, thereby eluting nucleic acids from mammalian cells or the like and indigenous enteric bacteria in the stool sample; and then, as a step (b), recovery of the eluted nucleic acids.

The denaturing of proteins in the stool sample in the step (a) can be carried out using a conventionally known technique. For example, by adding a compound generally used as a denaturing agent of proteins, such as a chaotropic salt, an organic solvent or a surface active agent, to the stool sample, proteins in the stool sample can be denatured. As the chaotropic salt or surface active agent to be added to the stool sample in the step (a), the same chaotropic salts and surface active agents as those mentioned earlier to be added to the solution for preparing a stool sample according to the present invention can be used. Phenol is preferable as the above organic solvent. Phenol may be neutral or acidic. When acidic phenol is used, it is possible to selectively extract RNA rather than DNA in an aqueous layer. Note that when adding a chaotropic salt, an organic solvent, a surface active agent or the like to the stool sample in the step (a), one type of compound may be added, or two or more types of compounds may be added.

Following the step (a) and prior to the step (b), as a step (c), the proteins denatured in the step (a) may be removed. By removing the denatured proteins before recovering nucleic acids, it is possible to improve the quality of recovered nucleic acids. The removal of proteins in the step (c) can be carried out using a conventionally known technique. For example, denatured proteins can be removed by precipitating the denatured proteins by centrifugation, followed by the collection of supernatant alone. In addition, rather than simply performing a centrifugal separation process, denatured proteins can even more thoroughly removed by first adding chloroform to a sample, and subsequently stirring and mixing the resultant sufficiently using a vortex mixer or the like, and the denatured proteins are then precipitated by centrifugation, followed by the collection of supernatant alone.

The recovery of the eluted nucleic acids in the step (b) can be carried out by a known technique such as an ethanol precipitation method and a cesium chloride ultracentrifugation method. Moreover, nucleic acids can be recovered by first, as a step (b1), making the nucleic acids eluted in the step (a) to adsorb to an inorganic substrate; and then, as a step (b2), eluting the nucleic acids adsorbed in the step (b1) from the inorganic substrate. As the inorganic substrate to which nucleic acids are adsorbed in the step (b1), a conventionally known inorganic substrate which is capable of adsorbing nucleic acids can be used. In addition, the shape of the inorganic substrate is not particularly limited, and it may be a particulate form or a membranous form. Examples of the inorganic substrate include silica-containing particles (beads) such as silica gel, siliceous oxide, glass and diatomaceous earth; and porous membranes made of nylon, polycarbonate, polyacrylate, and nitrocellulose.

As a solvent for eluting the adsorbed nucleic acids in the step (b2) from the inorganic substrate, a solvent generally used for eluting nucleic acids from conventionally known inorganic substrates can be used, where appropriate, depending on the type of recovered nucleic acids or the method for the following nucleic acid analysis. Purified water is particularly preferable as the solvent for elution. Note that it is preferable to wash the inorganic substrate to which nucleic acids are adsorbed with an appropriate washing buffer, following the step (b1) and prior to the step (b2).

It should be noted that when a stool sample is prepared using a solution for preparing a stool sample which contains a chaotropic salt or a surface active agent at a concentration sufficient for eluting nucleic acids from mammalian cells or the like, the step (a) can be omitted in the recovery of nucleic acids from the stool sample.

When a stool sample is prepared using a solution for preparing a stool sample which does not contain a chaotropic salt or a surface active agent at a concentration sufficient for eluting nucleic acids from mammalian cells or the like, as a step (d), it is preferable to recover a solid content from the stool sample prior to the step (a). In order to rapidly mix stool and the solution for preparing a stool sample, the stool sample contains a larger proportion of liquid components with respect to the solid content in the stool. Accordingly, by removing, from the stool sample, the solution for preparing a stool sample and then recovering only the solid content containing mammalian cells or the like and indigenous enteric bacteria, it is possible to reduce the scale of the samples used for recovering and analyzing nucleic acids. Moreover, by removing a water-soluble organic solvent from the solid content, it is also possible to suppress the adverse effects of the water-soluble organic solvent in the step for recovering nucleic acids from the solid content. For example, by centrifuging the stool sample of the present invention to precipitate the solid content therein and then removing the supernatant, the solid content alone can be recovered. Alternatively, it is also possible to recover the solid content alone by a filtration process or the like. Further, it is also preferable to wash the recovered solid content with an adequate buffer such as phosphate buffered saline (PBS, having a pH of 7.4).

Note that although a denaturing agent of proteins, such as a chaotropic salt, may be added directly to the recovered solid content, it is preferable to first suspend the solid content in an adequate medium and then add a denaturing agent of proteins thereto. When recovering DNA, as the medium for elution, for example, a phosphate buffer, a tris buffer, or the like can be used. It is preferable that DNase in the medium be deactivated by high pressure steam sterilization or the like, and it is more preferable that the medium contain a proteolytic enzyme such as Proteinase K. On the other hand, when recovering RNA, as the medium for elution, for example, a citrate buffer or the like can be used. However, since RNA is a material which is highly prone to degradation, it is preferable to use a buffer containing an RNase inhibitor, such as guanidine thiocyanate and guanidine hydrochloride.

Depending on the analytical methods used afterwards, the recovery of nucleic acids from the stool sample may not be needed. More specifically, after eluting nucleic acids from mammalian cells or the like and indigenous enteric bacteria in the stool sample, the sample can be directly used for the nucleic acid analysis. For example, when pathogenic bacteria and the like are present in large numbers in a stool sample and if the nucleic acids from the pathogenic bacteria were to be analyzed, it is possible to detect genes or the like originating from pathogenic bacteria by first recovering a solid content from the stool sample and then adding thereto a medium for the elution, such as PBS, which contains a proteolytic enzyme, such as Proteinase K, to mix, and finally using the obtained uniform solution of stool sample directly for the nucleic acid analysis. Alternatively, the recovery of nucleic acids from the stool sample can also be carried out by using a commercially available kit such as a nucleic acid extraction kit or a virus detection kit.

The nucleic acids recovered from the stool sample of the present invention can be analyzed using a conventionally known analytical method. Examples of the method for analyzing nucleic acids include a method for quantitating nucleic acids and a method for detecting specific base sequence regions using a polymerase chain reaction (PCR) or the like. In addition, when RNA is recovered, it is possible to first synthesize cDNA by reverse transcriptase polymerase chain reaction (RT-PCR), and then analyze the synthesized cDNA in the same manner as described above for the DNA analysis. For example, by detecting the presence and absence of genetic variations, such as a base sequence region in which a cancer gene or the like is encoded or a base sequence region containing microsatellites, it is possible to examine the development of cancers. When using the DNA recovered from the stool sample, for example, the analysis of mutations in the DNA or the analysis of epigenetic changes can be performed. Examples of the mutation analysis include the analyses of insertion, deletion, substitution, duplication and inversion of bases. Further, examples of the analysis of epigenetic changes include the analyses of methylation and demethylation. On the other hand, when using the recovered RNA, for example, it is possible to detect mutations, such as the insertion, deletion, substitution, duplication and inversion in the RNA base, and splicing variants (isoforms). In addition, the analyses of functional RNA (noncoding RNA), such as the analyses of, for example, transfer RNA (tRNA), ribosomal RNA (rRNA) and microRNA (miRNA), can be carried out. Furthermore, the level of RNA expression can also be detected and analyzed. It is particularly preferable to perform an mRNA expression analysis, a mutation analysis of K-ras gene, an analysis of DNA methylation, or the like. Note that these analyses can be carried out using the methods which are conventionally known in the field. Moreover, it is also possible to use a commercially available analysis kits such as a K-ras gene mutation analysis kit and a methylation detection kit.

By collecting stool in a stool collection container to which the solution for preparing a stool sample according to the present invention is added in advance, the collected stool can be prepared in an even more simple and rapid manner. In addition, by using a kit for collecting stool that includes both the solution for preparing a stool sample according to the present invention and a stool collection container containing the solution for preparing a stool sample, the effects of the present invention can be achieved more easily. Note that the kit for collecting stool may include a constituent other than the solution for preparing a stool sample and the stool collection container containing the solution, such as a stool collection rod, where appropriate.

The form or size of such stool collection container is not particularly limited, and known stool collection containers which may contain a solvent can be used. A stool collection container in which the lid of the stool collection container and a stool collection rod are integrated is preferable because it is easy to handle. In addition, because the amount of stool collection can be controlled, a container in which a stool collection rod may collect a certain amount of stool is more preferable.

Examples of such stool collection container which is already known include a stool collection container disclosed in Patent Document 7.

Figure 2:
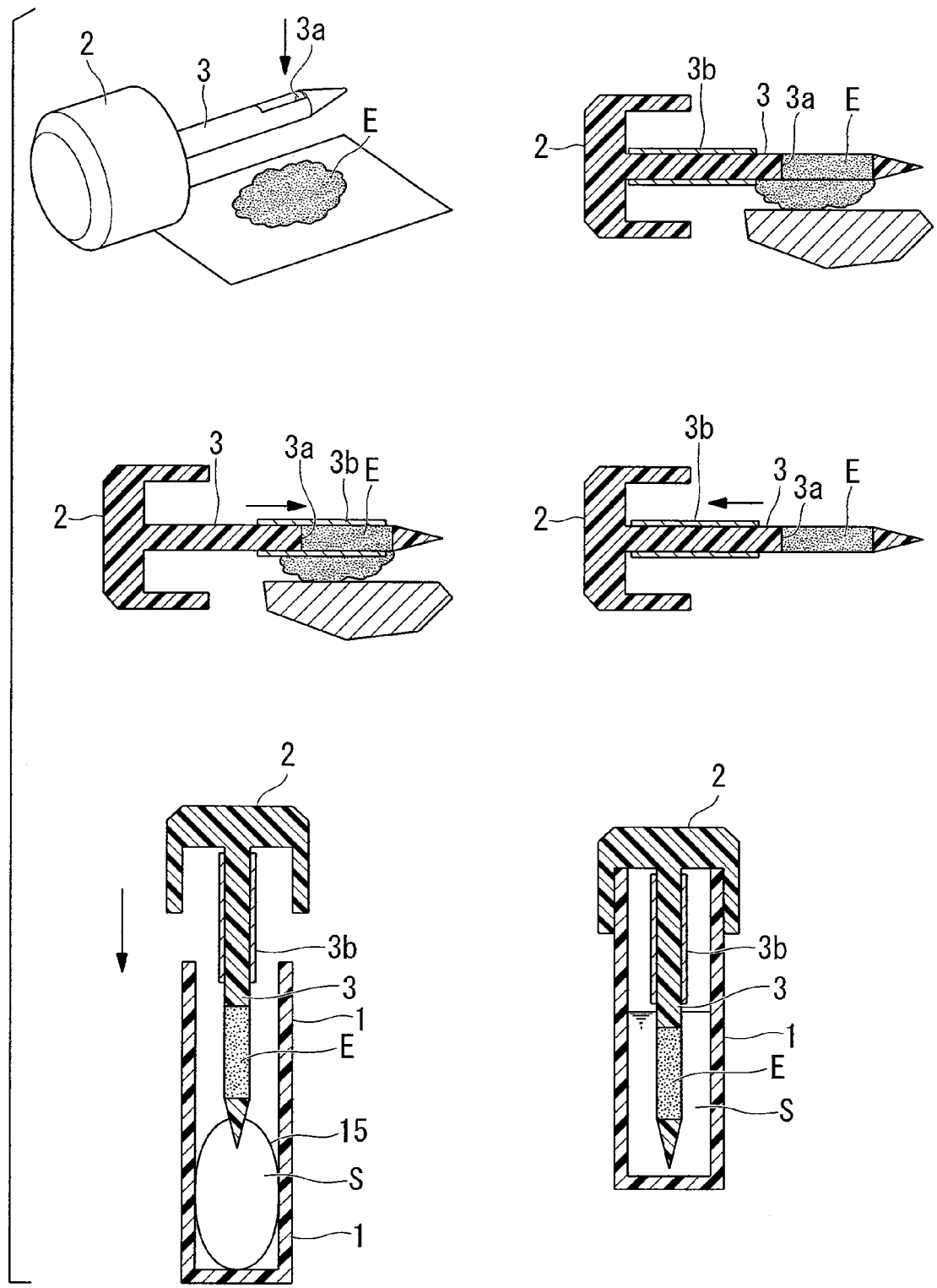
FIG. 2 is a diagram showing another aspect of a stool collection container which can be used for a kit for collecting stool according to the present invention.

FIGS. 1 and 2 are diagrams showing one aspect of a stool collection container which can be used for a kit for collecting stool according to the present invention. It should be noted that the stool collection containers which can be used for a kit for collecting stool according to the present invention are not limited to these stool collection containers.

First, a stool collection container in FIG. 1 will be described. The stool collection container includes a lid 2 which is integrated with a stool collection rod 3, and a container body 1, and contains the solution S for preparing a stool sample according to the present invention therein. A cup 3a which may collect a certain amount of stool is attached to the top end of the stool collection rod 3, and the cup 3a has sieve mesh. Meanwhile, a protruded portion 1a having a shape which is complementary to that of the cup 3a is present in the bottom of the container body 1. By fitting the cup 3a with the protruded portion 1a, the stool collected in the cup 3a is mechanically extruded from the sieve mesh in the cup 3a, and thus the stool can be rapidly dispersed in the solution S for preparing a stool sample.

The stool collection container depicted in FIG. 2 is a stool collection container that includes a lid 12 integrated with a stool collection rod 13 having a pointed end; a container body 11; and a bag 15, which is sealed and contains the solution S for preparing a stool sample according to the present invention, inside the container body 11. An orifice 13a for collecting a certain amount of stool E is provided in the stool collection rod 13. In addition, a movable lid 13b which may become a lid for the orifice 13a by sliding over the stool collection rod 13 is also attached. As shown in FIG. 2a, the movable lid 13b is first slid to the lid 12 side by passing the orifice 13a so as to leave the orifice 13a in a completely open state, and then the stool collection rod 13 is pressed against the stool E. Then, as shown in FIG. 2b, the orifice 13a is filled with the stool E. In this state, the movable lid 13b is slid to cover the orifice 13a, thereby accurately collecting the same volume of stool as that of the orifice 13a (FIG. 2c). Thereafter, the movable lid 13b is returned to the original position so as to make the orifice 13a in a completely open state (FIG. 2d), and then the lid 12 is housed in the container body 11 (FIG. 2e). When the stool collection rod 13 is housed in the container body 11, because the pointed end of the stool collection rod 13 breaks the bag 15 containing the solution S for preparing a stool sample, the solution S for preparing a stool sample and the stool E are mixed. Since such a stool collection container is filled with a solution only after the stool collection rod is placed inside the container, even when using a solution for preparing a stool sample which is harmful for the human body, such as methanol, accidents due to the solution leakage can be avoided, and thus the container can be handled safely even in general households.

Next, the present invention will be described in more detail based on a series of examples, although the scope of the present invention is in no way limited by the following examples. Note that "%" refers to "volume %", unless otherwise specified. In addition, Caco-2 cells, SW620 cells and MKN45 cells which were cultured cells, as well as the bacterial cells of *Enterobacter aerogenes* were cultured by ordinary methods.

EXAMPLE 1

Stool collected from one healthy individual was dispensed into three 15-mL polypropylene tubes (1 g each). Immediately after the dispensation, one polypropylene tube was quickly subjected to a freezing treatment using liquid nitrogen, thereby preparing a stool sample (1A). After the dispensation, 10 mL of 70% ethanol solution was added to one of the other polypropylene tubes. After sufficiently dispersing the stool in the solution, the tube was left to stand for 1 hour, thereby preparing a stool sample (1B). After the dispensation, the remaining one polypropylene tube was quickly transferred to an extraction step without adding any solutions or the like thereto, thereby preparing a stool sample (1C).

Thereafter, RNA was recovered from each stool sample. More specifically, 3 mL of a phenol mixture "Trizol" (manufactured by Invitrogen Corporation) was added to each stool sample, and the samples were sufficiently mixed for 30 seconds or more using a homogenizer, followed by the addition of 3 mL of chloroform. After sufficiently mixing the resultant by vortexing, the samples were centrifuged (12,000×g) at 4° C. for 20 minutes. The supernatant (aqueous layer) obtained as a result of the centrifugation was passed through an RNA recovery column of the RNeasy midi kit (manufactured by Qiagen GmbH), and RNA was recovered by the washing of the RNA recovery column followed by RNA extraction according to the protocol provided in the kit. The recovered RNA was quantified using the Nanoprop instrument (manufactured by Nanoprop Technologies, Inc.).

Figure 5:
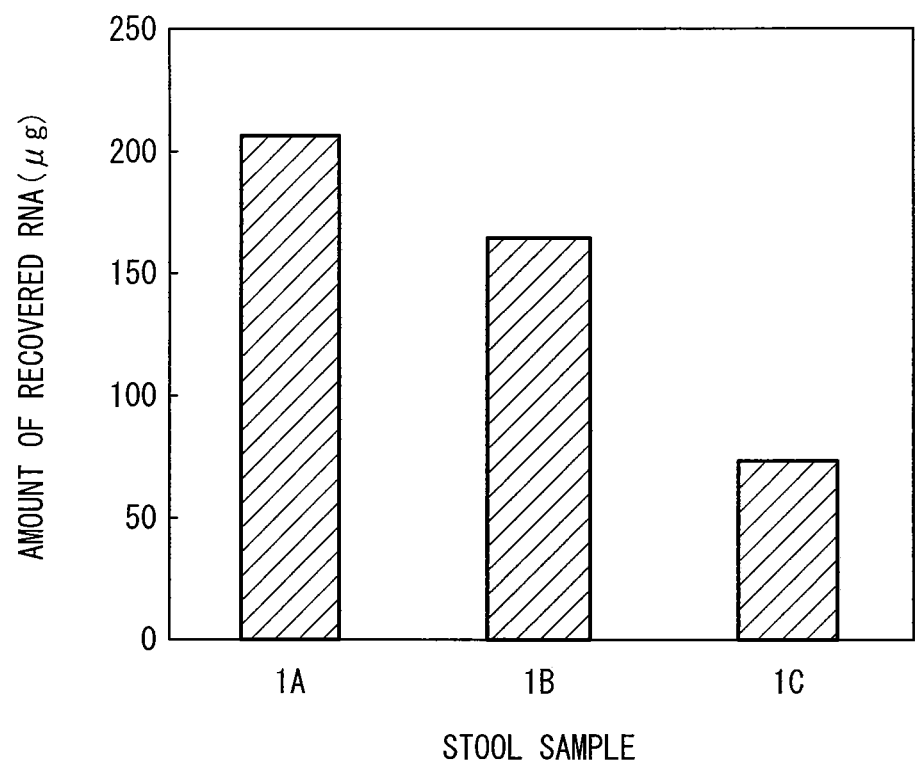
FIG. 5 is a diagram showing the amount of RNA recovered from each stool sample.

FIG. 5 is a diagram showing the amount of RNA recovered from each stool sample. From the stool sample (1B) prepared using an ethanol solution which was the solution of the present invention for preparing a stool sample, it was possible to recover a much larger amount of RNA, as compared to the stool sample (1C) in which nucleic acids were quickly extracted immediately after the stool collection, although it was slightly less than the amount of RNA recovered from the stool sample (1A) which was subjected to a freezing treatment immediately after the stool collection. From these results, it is evident that even when a preparation process is conducted at room temperature, by using the solution for preparing a stool sample according to the present invention in the preparation process, it is possible to obtain a stool sample from which nucleic acids may be recovered highly efficiently. In those cases where a patient is collecting stool at home for a checkup or the like, it is desirable that the preparation of stool samples can be carried out at a temperature close to room temperature. The solution for preparing a stool sample according to the present invention fully satisfies such a requirement.

EXAMPLE 2

0.5 g of stool from a healthy individual was mixed with 5.0×10$^5$ cells of a human colon cancer cell line (Caco-2 cells) which were expressing a high level of MDR1 (multidrug resistance 1) gene to prepare an artificial stool of colon cancer patients, and this artificial stool was used to prepare stool samples by the method for preparing a stool sample according to the present invention.

More specifically, the artificial stool of colon cancer patients was dispensed into 15-mL polypropylene tubes (0.5 g each), and the solutions for preparing a stool sample indicated in Table 1 were added to each tube and mixed, thereby preparing the stool samples. Note that the "universal collection medium" in the table refers to a preservation medium disclosed in Patent Document 4 which contains 500 mL of Puck's Saline G, 400 mg of sodium bicarbonate, 10 g of bovine serum albumin (BSA), 500 units/L of penicillin G, 500 mg/L of streptomycin sulfate, 1.25 mg/L of amphotericin B and 50 mg/L of gentamicin. The prepared stool samples were preserved in a constant temperature incubator set at room temperature (25° C.) for 1, 3, 7, and 10 days, respectively.

TABLE 1

| Solution for preparing stool sample | |
|---|---|
| (2A) | 5 mL of 70% methanol solution |
| (2B) | 1 mL of 100% methanol solution |
| (2C) | 5 mL of universal collection medium |
| (2D) | 5 mL of PBS |

Following preservation, RNA was recovered from each stool sample, and attempts were made in order to detect the transcription products (mRNA) of MDR1 gene from the recovered RNA. With respect to the stool sample prepared using the solution for preparing a stool sample (2C) (hereafter, referred to as the "stool sample (2C)"), mammalian cells including Caco-2 cells were first separated, followed by the RNA recovery. With respect to the stool samples prepared using the solutions for preparing a stool sample other than the solution for preparing a stool sample (2C), the nucleic acids originating from mammalian cells and the nucleic acids originating from bacteria were recovered at the same time without the separation of mammalian cells. The separation of mammalian cells from the stool sample (2C) was specifically conducted as follows. 5 mL of Histopack 1077 solution (manufactured by Sigma-Aldrich Corporation) was added to the stool sample (2C) and mixed, and the mixture was then centrifuged (200×g) at room temperature for 30 minutes, followed by the recovery of the interfacial portion between the suspension and the Histopack 1077 solution. The separated mammalian cells were washed three times with PBS.

The recovery of RNA from the stool samples was specifically conducted as follows. 3 mL of a phenol mixture "Trizol" (manufactured by Invitrogen Corporation) was first added to the stool sample (or to the separated mammalian cells, only for the case of the stool sample (2C)), and the samples were sufficiently mixed for 30 seconds or more using a homogenizer, followed by the addition of 3 mL of chloroform. Then, the resultant was centrifuged at 12,000×g for 10 minutes. The supernatant (aqueous layer) obtained as a result of the centrifugation was collected in a new polypropylene tube. Thereafter, RNA was recovered from the collected supernatant using the RNeasy midi kit (manufactured by Qiagen GmbH).

Reverse transcriptase polymerase chain reaction (RT-PCR) was performed using the recovered RNA, and PCR was then carried out using the obtained cDNA as a template. As primers, a base sequence for amplifying MDR1 gene which had a sequence number 1 and a base sequence for amplifying MDR1 gene which had a sequence number 2 were used as a forward primer and a reverse primer, respectively.

More specifically, to a 0.2-mL PCR tube, 12 pt of ultrapure water and 2 µL of a buffer (10×) were added, and 1 µL of cDNA, the forward primer, the reverse primer, magnesium chloride, dNTP, and DNA polymerase were each added thereto and mixed, thereby preparing a PCR reaction solution. PCR was carried out for 30 cycles, each amplification cycle consisted of incubating the PCR tubes at 95° C. for 30 seconds, 60° C. for 30 seconds, and then at 72° C. for 1 minute. The PCR products obtained as a result of the amplification was electrophoresed using the Agilent DNA 1000 LabChip (registered trade mark) kit (manufactured by Agilent Technologies, Inc.), and the intensity of the obtained band was measured, thereby examining the extent of amplification indicated by the PCR products.

TABLE 2

| | Preservation periods | | | |
|---|---|---|---|---|
| | 1 day | 3 days | 7 days | 10 days |
| Stool sample (2A) | ++ | ++ | ++ | + |
| Stool sample (2B) | ++ | ++ | + | + |
| Stool sample (2C) | − | − | − | − |
| Stool sample (2D) | − | − | − | − |

++: Intense level of amplification;
+: Intermediate level of amplification;
+/−: Weak level of amplification;
−: No amplification Table 2 summarizes the extent of amplification indicated by the PCR products which originated from each stool samples, based on different preservation periods. Note that in the table, "stool sample (2A)" refers to a stool sample prepared using a solution for preparing a stool sample (2A), "stool sample (2B)" refers to a stool sample prepared using a solution for preparing a stool sample (2B), and "stool sample (2D)" refers to a stool sample prepared using a solution for preparing a stool sample (2D), respectively.

As a result, with respect to the stool sample (2D), although the presence of amplified PCR products was confirmed when the sample preserved for 1 day was used, no amplification was observed when using the samples preserved for 3 days or longer. On the other hand, with respect to the stool samples (2A) and (2B) prepared using a solution for preparing a stool sample (2A) or a solution for preparing a stool sample (2B) which were the solutions for preparing stool samples according to the present invention, the presence of amplified PCR products was confirmed even when the samples preserved for 10 days were used. Meanwhile, with respect to the stool sample (2C) prepared using a solution for preparing a stool sample (2C) disclosed in Patent Document 4, no amplification of PCR products was observed even when using the sample preserved only for 1 day.

From the above results, it is evident that from the stool samples prepared by the preparation method according to the present invention, it is possible to efficiently recover nucleic acids contained in stool. In addition, by using the stool samples according to the present invention, it is also apparent that the accuracy for RNA analysis may also be improved. It is thought that this is because by using the solution for stool sample according to the present invention, the nucleic acids originating from mammalian cells that are contained in the stool and even RNA which is particularly prone to degradation, can be stably preserved for a long time at room temperature.

On the other hand, because no amplification of PCR products originating from the stool sample (2C) was observed, when a solution containing an antibiotic was used as the solution for preparing a stool sample, although bacterial cells will be killed by the antibiotic, it is possible that the RNA degradation may even be accelerated due to the release of RNase or the like from the dead bacterial cells. In addition, because the number of mammalian cells contained in stool is small, when the mammalian cells are separated from the stool, as compared to the method for recovering nucleic acids according to the present invention in which the nucleic acids originating from bacterial cells may function as a carrier, it is possible that sufficient amount of nucleic acids may be difficult to recover.

EXAMPLE 3

0.1 g of stool from a healthy individual was mixed with $1.0 \times 10^5$ cells of a human colon cancer cell line (SW620 cells) which were expressing a high level of Claudin-1 gene to prepare an artificial stool of colon cancer patients, and this artificial stool was used to prepare stool samples by the method for preparing a stool sample according to the present invention.

More specifically, 0.1 g of the artificial stool of colon cancer patients was dispensed into a 15-mL polypropylene tube, into which 1 mL of a 90% ethanol solution serving as a solution for preparing a stool sample was dispensed in advance, and the resultant was mixed by vortexing, thereby preparing a stool sample (3A). A sample prepared by using $1.0 \times 10^5$ cells of the SW620 cells alone, instead of the artificial stool of colon cancer patients, was used as a control sample. After leaving the prepared stool sample (3A) and control sample to stand for preservation at room temperature (25° C.) for 1 day, RNA was recovered from each sample, and attempts were made in order to detect the transcription products (mRNA) of Claudin-1 gene from the recovered RNA.

The recovery of RNA from each sample was specifically conducted as follows. 2 mL of a phenol mixture "ISOGEN" (manufactured by Nippon Gene Co., Ltd.) was first added to each stool sample (3A) and control sample, and the samples were sufficiently mixed for 30 seconds or more using a homogenizer, followed by the addition of 3 mL of chloroform. After sufficiently mixing the resultant by vortexing, the samples were centrifuged (12,000×g) at 4° C. for 20 minutes. The supernatant (aqueous layer) obtained as a result of the centrifugation was passed through an RNA recovery column of the RNeasy midi kit (manufactured by Qiagen GmbH), and RNA was recovered by the washing of the RNA recovery column followed by RNA extraction according to the protocol provided in the kit.

Note that in the above protocol, when 1 mL of a 90% ethanol solution and 2 mL of ISOGEN were mixed and the mixture was separated into a hydrophobic layer and an aqueous layer, because a portion of ethanol is transferred to the aqueous layer, it was possible to recover RNA by directly passing the obtained aqueous layer through the column. In a general protocol, a sample is dissolved in ISOGEN and then mixed with chloroform, and after separating an aqueous layer from the resulting mixture, the obtained aqueous layer is further mixed with an equal volume of 70% ethanol, and the resulting mixture is finally passed through a column. In other words, in the present example, the protocol became simpler compared to the general protocol.

Reverse transcriptase polymerase chain reaction (RT-PCR) was performed using the recovered RNA, and PCR was then carried out using the obtained cDNA as a template. As primers, a base sequence for amplifying Claudin-1 gene which had a sequence number 3 and a base sequence for amplifying Claudin-1 gene which had a sequence number 4 were used as a forward primer and a reverse primer, respectively. By conducting a PCR using the forward primer and reverse primer, PCR products of 233 bp can be obtained.

Figure 4:
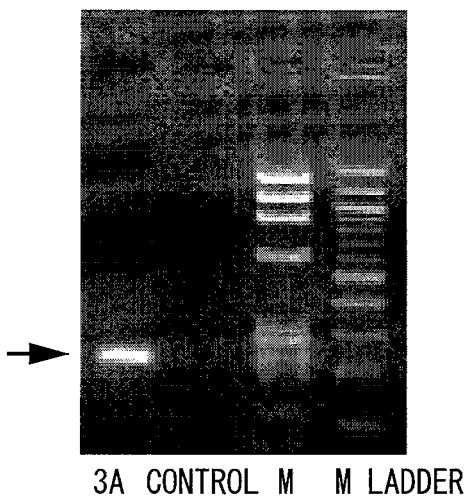
FIG. 4 is an image of the obtained PCR products stained with ethidium bromide following agarose gel electrophoresis in Example 3. In this figure, "3A" indicates a lane in which a PCR product originating from the stool sample (3A) is run, "control" indicates a lane in which a PCR product originating from the control sample is run, and "M" and "M ladder" indicate lanes in which markers are run. In addition, the arrow indicates a 233 bp band.

More specifically, to a 0.2-mL PCR tube, 12 μL of ultrapure water and 2 μL of a buffer (10×) were added, and 1 μL of cDNA, the forward primer, the reverse primer, magnesium chloride, dNTP, and DNA polymerase were each added thereto and mixed, thereby preparing a PCR reaction solution. PCR was carried out for 32 cycles, each amplification cycle consisted of incubating the PCR tubes at 95° C. for 30 seconds, 60° C. for 30 seconds, and then at 72° C. for 1 minute. FIG. 4 is an image of the obtained PCR products stained with ethidium bromide following agarose gel electrophoresis. In this figure, "3A" indicates a lane in which a PCR product originating from the stool sample (3A) is run, "control" indicates a lane in which a PCR product originating from the control sample is run, and "M" and "M ladder" indicate lanes in which markers are run. In addition, the arrow indicates a 233 bp band.

Although both the stool sample (3A) and control sample contained equal amount of SW620 cells, as is apparent from FIG. 4, although amplified products of 233 bp were detected in the PCR products originated from the stool sample (3A), no such products were detected in the PCR products originated from the control sample. It is thought that in the stool sample (3A), since the nucleic acids originated from the SW620 cells, which were assumed to be the cells exfoliated from the large intestine, and the nucleic acids originated from bacterial cells in the stool were recovered at the same time, the nucleic acids originated from bacterial cells functioned as a carrier, thereby efficiently recovering the nucleic acids originated from the SW620 cells. On the other hand, it is thought that in the control sample, because the number of cells was low with only the SW620 cells being present, it was not possible to recover a sufficient amount of RNA for the nucleic acid analysis.

From the results above, it is apparent that by the method for recovering nucleic acids according to the present invention in which the nucleic acids originating from mammalian cells and nucleic acids originating from bacterial cells in the stool sample are recovered at the same time, it is possible to efficiently recover the nucleic acids originating from mammalian cells from the stool sample.

EXAMPLE 4

$1.0 \times 10^6$ cells of a facultative anaerobe (*Enterobacter aerogenes*) and $0.5 \times 10^6$ cells of MKN45 cells were mixed with 1 mL of PBS to prepare an artificial stool, and a stool sample was prepared by the method for preparing a stool sample according to the present invention using the artificial stool. Note that *Enterobacter aerogenes* is an indigenous enteric bacterium that usually exists inside the human intestine, and is usually harmless to humans.

More specifically, 1 mL of the artificial stool was dispensed into a 15-mL polypropylene tube, into which 5 mL of a 50% methanol solution serving as a solution for preparing a stool sample was dispensed in advance, and the resultant was mixed by vortexing, thereby preparing a stool sample (4A). A sample prepared by mixing $0.5 \times 10^6$ cells of the MKN45 cells alone, instead of the artificial stool, with 1 mL of PBS was used as a control sample. After preserving the prepared stool sample (4A) and control sample at room temperature for 3 days, DNA was recovered from each sample, and attempts were made in order to detect the human GAPDH (Glyceraldehyde-3-phosphate dehydrogenase) gene from the recovered DNA.

The recovery of DNA from each sample was specifically conducted as follows. First, each sample was centrifuged at 1,000×g for 5 minutes, and the resulting supernatant was removed to recover precipitates (solid components). Thereafter, DNA was recovered from the obtained precipitates using the DNeasy Blood and Tissue Kit (manufactured by Qiagen GmbH).

PCR was then carried out using the recovered DNA as a template. As primers, a base sequence for amplifying human GAPDH (Glyceraldehyde-3-phosphate dehydrogenase) gene which had a sequence number 5 and a base sequence for amplifying human GAPDH gene which had a sequence number 6 were used as a forward primer and a reverse primer, respectively.

More specifically, the recovered DNA was first dispensed (2 μL each) into a 96-well microplate (n=3). Thereafter, 6 μL of ultrapure water and 10 μL of a nucleic-acid amplifying reagent (Geneamp PCR Master Mix, manufactured by Applied Biosystems, Inc.) were added to each well, 1 μL of the forward primer, reverse primer, a 500-fold diluted solution of CYBR Green reagent (manufactured by Invitrogen Corporation) were each added thereto and mixed, thereby preparing PCR reaction solutions. PCR was carried out for 32 cycles, each amplification cycle consisted of incubating the 96-well microplate at 95° C. for 30 seconds, 60° C. for 30 seconds, and then at 72° C. for 1 minute, while measuring the fluorescence intensity over time. The PCR products obtained by carrying out a PCR using the lambda phage DNA having a known concentration as a template were prepared as a positive control. By analyzing the results of fluorescence intensity measurements, the average amount of the GAPDH gene in the DNA recovered from each sample was calculated. As a result, the amount of GAPDH gene in the DNA recovered from the stool sample (4A) had an average of about 160 μg/μL, whereas the amount of GAPDH gene in the DNA recovered from the control sample had an average of about 30 μg/μL.

From the above results, it is evident that by using the method for preparing a stool sample according to the present invention and the method for recovering nucleic acids according to the present invention, it may be possible to efficiently recover nucleic acids originating from mammalian cells.

EXAMPLE 5

Ethanol solutions of 0%, 10%, 20%, 30%, 40%, 50%, 60%, 70%, 80%, 90% and 100% were prepared by dilution using ultrapure water. 5 mL of each of these ethanol solutions was dispensed into 15-mL polypropylene tube.

After dispensing 0.5 g of stool collected from a healthy individual to each of these tubes, the tubes were left to stand at 37° C. for 48 hours. Thereafter, each tube was centrifuged, and the resulting supernatant was removed to obtain a solid component. 3 mL of a phenol mixture "Trizol" (manufactured by Invitrogen Corporation) was added to the obtained solid components, and the samples were sufficiently mixed for 30 seconds or more using a homogenizer, followed by the addition of 3 mL of chloroform. Then, the resultant was centrifuged at 12,000×g for 10 minutes. The supernatant (aqueous layer) obtained as a result of the centrifugation was collected in a new polypropylene tube. Thereafter, RNA was recovered from the collected supernatant using the RNeasy midi kit (manufactured by Qiagen GmbH).

Figure 3:
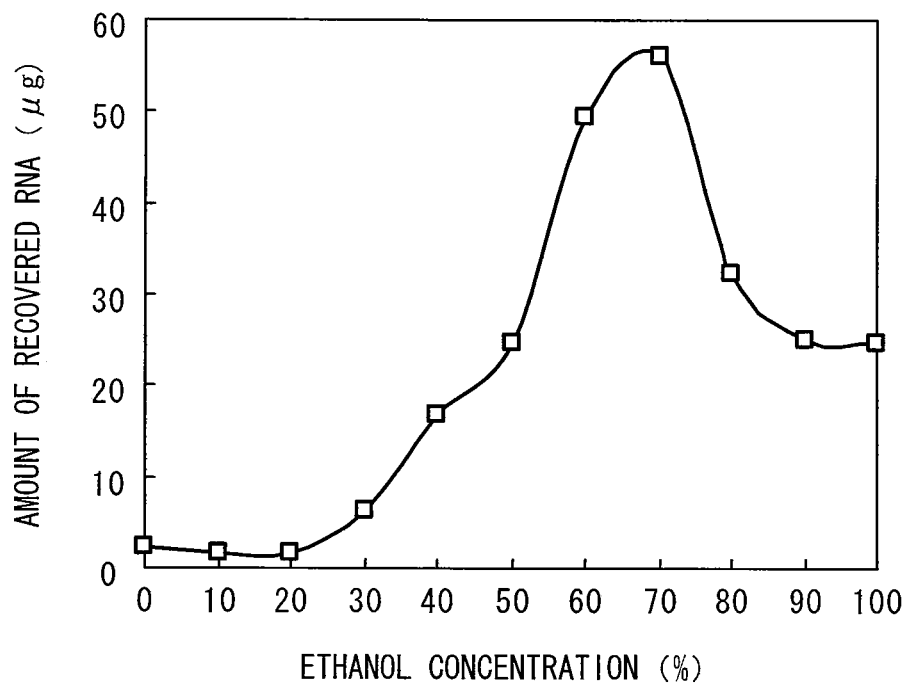
FIG. 3 is a diagram showing the amount of RNA recovered from stool samples prepared using ethanol solutions of each concentration in Example 5.

FIG. 3 is a diagram showing the amount of RNA recovered from stool samples prepared using ethanol solutions of each concentration. As a result, it is clear that when an alcohol such as ethanol is used as an active ingredient of the solution for preparing a stool sample, the alcohol concentration is preferably at least 30%, more preferably at least 50%, still more preferably within a range from 50 to 80%, and most preferably within a range from 60 to 70%.

EXAMPLE 6

Stool collected from five healthy individuals was mixed adequately and was then dispensed into two 15-mL polypropylene tubes (0.2 g each). 1 mL of a 32% modified ethanol solution containing 18% of isopropanol (having a total alcohol concentration of 50%) was added to one of the polypropylene tubes and mixed adequately, and the tube was then left to stand at 25° C. for 1 day. The prepared stool sample was used as a stool sample (6A). One of the remaining polypropylene tubes was used as a control sample, and was quickly transferred to a deep freezer set at −80° C. after the dispensation.

DNA was recovered from both stool samples using the QIAamp DNA Stool Mini Kit (manufactured by Qiagen GmbH) which was a DNA extraction kit from stool. The concentration of the recovered DNA was quantified by spectrophotometry. As a result, it was possible to recover almost the same amount of DNA from both stool samples.

A mutation analysis was conducted, using 100 ng of the recovered DNA as well as the "K-ras codon 12 mutations detection reagent" (manufactured by Wakunaga Pharmaceutical Co., Ltd.) which was a kit for analyzing mutations in the K-ras gene, and following the protocol attached to the kit. As a result, the analyses of DNA recovered from the stool sample (6A) against 6 types of mutated genes were all negative, as was the case where the DNA recovered from the control sample was used.

From the above results, it is evident that by using the nucleic acids recovered by the method for preparing a stool sample according to the present invention and the method for recovering nucleic acids according to the present invention, even the analyses of nucleic acids which require a high level of accuracy, such as the analyses of gene mutations, can be carried out with an adequate level of accuracy. In addition, although modified ethanol prepared by mixing isopropanol and ethanol was used in the present example as a process solution, equivalent results were obtained even when a 50% ethanol solution which had the same alcohol concentration as that of the modified ethanol was used.

EXAMPLE 7

0.5 g of stool from a healthy individual was mixed with $5.0 \times 10^5$ cells of a human colon cancer cell line (SW480 cells) which had a methylated site in the promoter region of the p16 gene to prepare an artificial stool of colon cancer patients, and this artificial stool was used to prepare stool samples by the method for preparing a stool sample according to the present invention.

More specifically, 0.5 g of the artificial stool of colon cancer patients was dispensed into a 15-mL polypropylene tube, into which 5 mL of a 70% ethanol solution serving as a solution for preparing a stool sample was dispensed in advance, and the resultant was mixed by vortexing, thereby preparing a stool sample (7A). In addition, 0.5 g of stool from a healthy individual was dispensed, instead of the artificial stool, into a 15-mL polypropylene tube, into which 5 mL of a 70% ethanol solution was dispensed in advance, and the resultant was mixed to prepare a control sample. DNA was recovered from each sample, and attempts were made in order to detect the methylation within the promoter region of the p16 gene from the recovered DNA.

The recovery of DNA from each sample was specifically conducted as follows. First, each sample was centrifuged at 1,000×g for 5 minutes, and the resulting supernatant was removed to recover precipitates (solid components). Thereafter, DNA was recovered from the obtained precipitates using the DNeasy Blood and Tissue Kit (manufactured by Qiagen GmbH). The recovered DNA was treated with bisulfite using the CpGenome Fast DNA Modification Kit (manufactured by Chemicon International, Inc.) which was a DNA methylation detection kit, and was subsequently amplified using the CpG Wiz p16 Amplification Kit (manufactured by Chemicon International, Inc.), and the presence of amplified products was verified by agarose gel electrophoresis. Each treatment was conducted by following the standard protocols provided with the above products.

As a result, although no methylation was detected from the control sample, it was possible to detect methylations from the stool sample (7A).

EXAMPLE 8

A stool sample was prepared and nucleic acids were recovered using a stool collection container as shown in FIG. 1. The stool collection container includes a lid 2 which is integrated with a stool collection rod 3, and a container body 1, and contains 5 mL of a 70% 1-isopropanol solution therein, and a cup 3a having a volume of 0.5 mL and including 4 holes that have a diameter of 3 mm is attached to the top end of the stool collection rod 3.

First, about 0.5 g of stool was collected in the cup 3a using the stool collection rod 3, and was placed in the stool collection container, which was closed with the lid 2. Then, a protruded portion 1a in the bottom of the container body 1 extruded the stool in the cup 3a, and the stool was mechanically extruded from the holes in the cup 3a and was rapidly dispersed in the solution. The stool sample prepared in such a manner was used as a stool sample (8A).

On the other hand, about 0.5 g of stool was collected in a 15-mL polypropylene tube containing 5 mL of a 70% 1-isopropanol solution so that, just like the stool sample (8A), the volume ratio of the stool and the solution for preparing a stool sample was 1:10, and the tube was then left to stand, thereby preparing a control sample.

After preserving the stool sample (8A) and control sample at room temperature for 1 week, RNA was recovered in the same manner as described in Example 5. As a result, it was possible to recover about 210 μg of RNA and about 150 μg of RNA from the stool sample (8A) and control sample, respectively. It is thought that by using the stool collection container as shown in FIG. 1, it was possible to rapidly disperse stool in the solution for preparing a stool sample, and thereby to recover nucleic acids with even higher efficiency.

EXAMPLE 9

A stool sample was prepared and nucleic acids were recovered using a stool collection container as shown in FIG. 2. The stool collection container is a stool collection container that includes a lid 12 integrated with a stool collection rod 13 having a pointed end and an orifice that has a volume of 0.5 mL; a container body 11; and a bag 15, which is sealed and contains a 59% methanol solution, inside the container body 11.

First, by using a stool collection container containing 5 mL of a 59% methanol solution in the bag 15, about 0.5 g of stool was collected and mixed with the 59% methanol solution following the procedures depicted in FIG. 2, thereby preparing a stool sample (9A). On the other hand, a stool sample (9B) was prepared in the same manner as that described for preparing the stool sample (9A), except that a stool collection container containing 0.5 mL of a 59% methanol solution in the bag 15 was used.

RNA was recovered from the stool sample (9A) and stool sample (9B) in the same manner as described in Example 5. As a result, the amount of recovered RNA was about 120 μg and about 80 μg from the stool sample (9A) and stool sample (9B), respectively, and thus it was possible to recover a sufficient amount of RNA from both samples, as compared to those prepared by conventional methods. From the results of stool sample (9A), it is evident that by preparing a stool sample by using a sufficient amount of solution for preparing a stool sample, with respect to the amount of stool, it may be possible to recover nucleic acids with even higher efficiency.

On the other hand, as is apparent from the results of stool sample (9B), because nucleic acids can be efficiently recovered using the preparation method of the present invention, it becomes possible to reduce the weight and size of the kit for collecting stool.

EXAMPLE 10

Stool collected from one healthy individual was dispensed into three 15-mL polypropylene tubes (0.1 g each). 3 mL of a 70% ethanol solution was added to one of the polypropylene tubes to sufficiently disperse the stool, and the obtained stool sample was used as a stool sample (10A). On the other hand, to the remaining two polypropylene tubes, 2.4 mL of "ISOGEN" (manufactured by Nippon Gene Co., Ltd.) was each added to sufficiently disperse the stool, and the obtained stool samples were used as comparative samples (P1) and (P2). It should be noted that "ISOGEN" is a phenol-containing material that contains 40% of phenol (having a water solubility of about 10% by weight).

Of the prepared comparative samples, RNA was rapidly recovered from the comparative sample (P1) following the stool dispersion. More specifically, the stool sample was sufficiently mixed for 30 seconds or more using a homogenizer, followed by the addition of 3 mL of chloroform. Then, the resultant was centrifuged at 12,000×g for 10 minutes. The supernatant (aqueous layer) obtained as a result of the centrifugation was collected in a new polypropylene tube. Thereafter, RNA was recovered from the collected supernatant using the RNeasy midi kit (manufactured by Qiagen GmbH).

Further, as for the comparative sample (P2), RNA was recovered in the same manner as that described for the comparative sample (P1), after leaving the sample to stand at room temperature for 5 hours.

On the other hand, the stool sample (10A) was left to stand at room temperature for 5 hours, just like the comparative sample (P2). Then the stool sample (10A) was centrifuged and the resulting supernatant was removed to obtain precipitates (solid components). RNA was recovered in the same manner as that described for the comparative sample (P1), after adding 2.4 mL of "ISOGEN" to the obtained precipitates.

The recovered RNA was quantified using the NanoDrop instrument (manufactured by NanoDrop Technologies, Inc.). As a result, although it was possible to recover 32 μg of RNA from the comparative sample (P1) with which the RNA recovery was conducted immediately after the preparation of stool sample, only 14 μg of RNA was recovered from the comparative sample (P2) with which the RNA recovery operation was conducted after leaving the sample to stand at room temperature for 5 hours. On the other hand, from the stool sample (10A), although the RNA recovery operation was conducted after leaving the sample to stand at room temperature for 5 hours, it was possible to recover 57 μg of RNA, which was far more than the amount of RNA recovered from the comparative sample (P1).

From these results, it is clear that by using the solution for preparing a stool sample according to the present invention, RNA may be recovered highly efficiently, as compared to the conventional cases where a phenol solution was used.

INDUSTRIAL APPLICABILITY

Since a stool sample can be prepared in a simple and easy manner, from which nucleic acids may be efficiently recovered, by using the method for preparing a stool sample according to the present invention, the preparation method can be used especially in the field of clinical laboratory tests, such as the routine checkups using stool samples.

The invention claimed is:
1. A method for recovering an RNA, comprising:
(a) dispersing stool collected from a subject in a solution having a water-soluble alcohol as an active ingredient, thereby producing a mixture, then recovering a solid content from the mixture, and then washing the recovered solid content with an adequate buffer, then
   (a-1) denaturing proteins in the washed solid content using a chaotropic salt, thereby eluting an RNA originating from indigenous enteric bacterium and an RNA originating from an organism other than indigenous enteric bacterium from the mixture,
(b) centrifuging the RNA originating from indigenous enteric bacterium and the RNA originating from an organism other than indigenous enteric bacterium of step (a-1) at the same time, and recovering precipitates therefrom.

2. The method for recovering an RNA according to claim 1, wherein the mixture is mixed by inversion or shaking after the dispersing of stool in the solution in step (a), and prior to the recovering of the solid content from the mixture.

3. The method for recovering an RNA according to claim 1, wherein the RNA originating from an organism other than indigenous enteric bacterium is an RNA originating from a mammalian cell.

4. The method for recovering an RNA according to claim 1, further comprising, following the step (a-1) and prior to the step (b),
(a-2) removing the proteins denatured in the step (a-1).

5. The method for recovering an RNA according to claim 4, wherein
removal of denatured proteins in the step (a-2) is carried out using chloroform.

6. The method for recovering an RNA according to claim 1, wherein the step (b) includes:
   (b-1) making the RNA that is eluted in the step (a-1) adsorb to an inorganic substrate; and
   (b-2) eluting the RNA adsorbed in the step (b-1) from the inorganic substrate.

7. The method for recovering an RNA according to claim 1, further comprising, prior to the step (a-1),
recovering a solid content from the mixture,
wherein step (a-1) is a step of denaturing proteins in the recovered solid content.

8. The method for recovering an RNA according to claim 1, wherein the concentration of the water-soluble alcohol in the solution is in a range from 50% to 80%.

9. The method for recovering an RNA according to claim 1, wherein the solution further includes an organic solvent.

10. The method for recovering an RNA according to claim 9, wherein the organic solvent is phenol.

11. The method for recovering an RNA according to claim 1, wherein the solution further includes a surface active agent.

12. The method for recovering an RNA according to claim 1, wherein the mixture is mixed by inversion or shaking after the dispersing of stool in the solution in step (a), and prior to the denaturing of the proteins in step (a-1).

* * * * *

SEQUENCE LISTING

<160> NUMBER OF SEQ ID NOS: 6

<210> SEQ ID NO 1
<211> LENGTH: 20

```
<212> TYPE: DNA
<213> ORGANISM: Artificial Sequence
<220> FEATURE:
<223> OTHER INFORMATION: Description of Artificial Sequence: primer.

<400> SEQUENCE: 1
tcattcgagt agcggctctt                                              20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: primer.

<400> SEQUENCE: 2
cttctttgct cctccattgc                                              20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: primer.

<400> SEQUENCE: 3
ccgttggcat gaagtgtatg                                              20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: primer.

<400> SEQUENCE: 4
aaggcagaga gaagcagcag                                              20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: primer.

<400> SEQUENCE: 5
cgaccacttt gtcaagctca                                              20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: primer.

<400> SEQUENCE: 6
aggggtctac atggcaactg                                              20
```